United States Patent
Edgett et al.

(10) Patent No.: US 9,192,522 B2
(45) Date of Patent: Nov. 24, 2015

(54) TAMPON ASSEMBLY HAVING SHAPED PLEDGET

(75) Inventors: Keith Edgett, Middletown, DE (US); Robert Jorgensen, Middletown, DE (US); Eugene P. Dougherty, Camden, DE (US)

(73) Assignee: Eveready Battery Company, INC., St. Louis, MO (US)

( * ) Notice: Subject to any disclaimer, the term of this patent is extended or adjusted under 35 U.S.C. 154(b) by 777 days.

(21) Appl. No.: 11/713,974

(22) Filed: Mar. 5, 2007

(65) Prior Publication Data

US 2007/0167902 A1    Jul. 19, 2007

Related U.S. Application Data

(63) Continuation-in-part of application No. 10/834,386, filed on Apr. 28, 2004.

(60) Provisional application No. 60/467,482, filed on May 2, 2003.

(51) Int. Cl.
*A61F 13/20* (2006.01)
*A61F 13/26* (2006.01)
*A61F 13/15* (2006.01)

(52) U.S. Cl.
CPC .............. *A61F 13/266* (2013.01); *A61F 13/208* (2013.01); *A61F 13/2022* (2013.01); *A61F 2013/15365* (2013.01); *A61F 2013/15422* (2013.01)

(58) Field of Classification Search
CPC ......... A61F 13/20; A61F 13/15; A61F 15/00; A61F 13/2022; A61F 13/208; A61F 13/26; A61M 31/00; A61H 7/00

USPC .............. 604/15, 14, 18, 385.17, 385.18, 904
See application file for complete search history.

(56) References Cited

U.S. PATENT DOCUMENTS

| | | |
|---|---|---|
| 1,191,736 A | 7/1916 | Roberson |
| 1,218,478 A | 3/1917 | Sappington |
| 1,554,690 A | 9/1925 | Pride |
| 1,555,708 A | 9/1925 | Gale |
| 1,731,665 A | 10/1929 | Huebsch |
| 2,077,231 A | 4/1937 | Fourness et al. |
| 2,095,377 A | 10/1937 | Breese |
| 2,099,931 A | 11/1937 | Fourness |
| 2,123,750 A | 7/1938 | Schulz |

(Continued)

FOREIGN PATENT DOCUMENTS

| | | |
|---|---|---|
| AU | 8774659 | 1/1988 |
| BE | 667613 | 1/1966 |

(Continued)

OTHER PUBLICATIONS

Retrieved from the internet on Mar. 3, 2010: http://www.merriam-webster.com/dictionary/slit.*

(Continued)

*Primary Examiner* — Jacqueline Stephens
(74) *Attorney, Agent, or Firm* — Edgewell Personal Care, LLC

(57) ABSTRACT

The present invention provides a tampon applicator assembly having an applicator barrel with an insertion tip with a maximum of three petals. Additionally, the tampon applicator assembly can be provided with a tapered insertion tip. A shaped pledget can be housed in the applicator barrel, which provides support to the petals.

41 Claims, 3 Drawing Sheets

(56) References Cited

U.S. PATENT DOCUMENTS

| | | |
|---|---|---|
| 2,178,704 A | 11/1939 | Robinson |
| 2,222,088 A | 11/1940 | Petersen |
| 2,254,272 A | 9/1941 | Crockford |
| 2,301,868 A | 11/1942 | Gurley, Jr. et al. |
| 2,306,406 A | 12/1942 | Robinson |
| 2,386,590 A | 10/1945 | Calhoun |
| 2,413,480 A | 12/1946 | Winter |
| 2,458,685 A | 1/1949 | Crockford |
| 2,476,956 A | 7/1949 | Bonham |
| 2,489,502 A | 11/1949 | Ruth |
| 2,499,414 A | 3/1950 | Rabell |
| 2,499,444 A | 3/1950 | Allison |
| 2,607,346 A | 8/1952 | Milcent |
| 2,706,986 A | 4/1955 | Carrier |
| 2,799,055 A | 7/1957 | Carrier |
| 2,854,978 A | 10/1958 | Millman et al. |
| 2,877,767 A | 3/1959 | Kramer |
| 2,905,175 A | 9/1959 | Schwartz |
| 3,204,635 A | 9/1965 | Voss et al. |
| 3,264,691 A | 8/1966 | Whitehead |
| 3,291,130 A | 12/1966 | Whitehead |
| 3,306,294 A | 2/1967 | Penksa |
| 3,306,295 A | 2/1967 | Penksa |
| 3,347,234 A | 10/1967 | Voss |
| 3,358,354 A | 12/1967 | Voss et al. |
| 3,369,544 A | 2/1968 | Crockford |
| 3,397,695 A | 8/1968 | Voss |
| 3,431,909 A | 3/1969 | Krusko |
| 3,431,910 A | 3/1969 | Kokx |
| 3,433,225 A | 3/1969 | Voss et al. |
| 3,520,302 A | 7/1970 | Jones |
| 3,570,489 A | 3/1971 | Brown |
| 3,572,341 A | 3/1971 | Glassman |
| 3,575,169 A | 4/1971 | Voss et al. |
| 3,595,236 A | 7/1971 | Corrigan |
| 3,628,533 A | 12/1971 | Loyer |
| 3,643,661 A | 2/1972 | Crockford |
| 3,683,915 A | 8/1972 | Voss |
| 3,690,321 A | 9/1972 | Hirschman |
| 3,695,270 A | 10/1972 | Dostal |
| 3,706,311 A | 12/1972 | Kokx et al. |
| 3,710,793 A | 1/1973 | Glassman |
| 3,712,305 A | 1/1973 | Wennerblom et al. |
| 3,726,277 A | 4/1973 | Hirschman |
| 3,731,687 A | 5/1973 | Glassman |
| 3,738,364 A | 6/1973 | Brien et al. |
| 3,762,413 A | 10/1973 | Hanke |
| 3,765,416 A | 10/1973 | Werner et al. |
| 3,794,029 A | 2/1974 | Dulle |
| 3,812,856 A | 5/1974 | Duncan et al. |
| 3,834,389 A | 9/1974 | Dulle |
| 3,845,767 A | 11/1974 | Friese et al. |
| 3,856,013 A | 12/1974 | Dulle |
| 3,858,571 A | 1/1975 | Rudolph |
| 3,885,563 A | 5/1975 | Johnson et al. |
| 3,905,372 A | 9/1975 | Denkinger |
| 3,946,737 A | 3/1976 | Kobler |
| 3,954,104 A | 5/1976 | Kraskin et al. |
| 3,971,378 A | 7/1976 | Krantz |
| 3,981,305 A | 9/1976 | Ring |
| 3,983,873 A | 10/1976 | Hirschman |
| 3,994,298 A | 11/1976 | Des Marais |
| 4,010,751 A | 3/1977 | Ring |
| 4,018,255 A | 4/1977 | Diggs |
| 4,027,673 A | 6/1977 | Poncy et al. |
| 4,048,998 A | 9/1977 | Nigro |
| 4,077,408 A | 3/1978 | Murray et al. |
| 4,077,409 A | 3/1978 | Murray et al. |
| 4,099,976 A | 7/1978 | Kraskin et al. |
| 4,108,180 A | 8/1978 | Moehrle |
| D250,663 S | 12/1978 | Koch et al. |
| 4,175,467 A | 11/1979 | Lashley |
| 4,185,631 A | 1/1980 | McConnell |
| 4,186,742 A | 2/1980 | Donald |
| 4,198,978 A | 4/1980 | Nigro |
| 4,211,225 A | 7/1980 | Sibalis |
| 4,212,301 A | 7/1980 | Johnson |
| 4,217,900 A | 8/1980 | Wiegner et al. |
| 4,266,546 A | 5/1981 | Roland et al. |
| 4,271,835 A | 6/1981 | Conn et al. |
| 4,274,412 A | 6/1981 | Austin |
| 4,278,088 A | 7/1981 | Reeves et al. |
| 4,291,696 A | 9/1981 | Ring |
| 4,294,253 A | 10/1981 | Friese |
| 4,308,867 A | 1/1982 | Roseman et al. |
| 4,309,997 A | 1/1982 | Donald |
| 4,312,348 A | 1/1982 | Friese |
| 4,318,407 A | 3/1982 | Woon |
| 4,328,804 A | 5/1982 | Shimatani |
| 4,335,720 A | 6/1982 | Glassman |
| 4,335,721 A | 6/1982 | Matthews |
| 4,341,211 A | 7/1982 | Kline |
| 4,341,214 A | 7/1982 | Fries et al. |
| 4,351,339 A | 9/1982 | Sneider |
| 4,361,150 A | 11/1982 | Voss |
| 4,361,151 A | 11/1982 | Fitzgerald |
| 4,421,504 A | 12/1983 | Kline |
| 4,424,054 A | 1/1984 | Conn et al. |
| 4,428,370 A | 1/1984 | Keely |
| 4,475,911 A | 10/1984 | Gellert |
| D279,504 S | 7/1985 | Tump |
| 4,536,178 A | 8/1985 | Lichstein et al. |
| 4,543,086 A | 9/1985 | Johnson |
| 4,543,098 A | 9/1985 | Wolfe et al. |
| 4,553,965 A | 11/1985 | Conn et al. |
| D287,876 S | 1/1987 | Blatherwick et al. |
| 4,676,773 A | 6/1987 | Sheldon |
| 4,726,805 A | 2/1988 | Sanders, III |
| 4,743,237 A | 5/1988 | Sweere |
| 4,755,166 A | 7/1988 | Olmstead |
| 4,845,922 A | 7/1989 | Sweere |
| 4,846,802 A | 7/1989 | Sanders, III |
| 4,891,042 A | 1/1990 | Melvin et al. |
| 5,019,061 A | 5/1991 | Hoden et al. |
| 5,047,024 A | 9/1991 | Glassman |
| 5,084,038 A | 1/1992 | Sheldon et al. |
| 5,112,348 A | 5/1992 | Glassman |
| 5,153,971 A | 10/1992 | Van Iten |
| 5,158,535 A | 10/1992 | Paul et al. |
| 5,213,566 A | 5/1993 | Weissenburger |
| 5,267,953 A | 12/1993 | Paul et al. |
| 5,279,541 A | 1/1994 | Frayman et al. |
| 5,342,331 A | 8/1994 | Silber et al. |
| 5,350,371 A | 9/1994 | Van Iten |
| 5,370,633 A | 12/1994 | Villalta |
| 5,387,206 A | 2/1995 | Valentine et al. |
| 5,395,308 A | 3/1995 | Fox et al. |
| 5,403,300 A | 4/1995 | Howarth |
| 5,417,224 A | 5/1995 | Petrus et al. |
| 5,437,628 A | 8/1995 | Fox et al. |
| 5,445,605 A | 8/1995 | Plüss |
| 5,542,914 A | 8/1996 | Van Iten |
| 5,547,701 A | 8/1996 | Nielsen et al. |
| 5,554,108 A | 9/1996 | Browning et al. |
| 5,584,827 A | 12/1996 | Korteweg et al. |
| 5,592,725 A | 1/1997 | Brinker |
| 5,634,248 A | 6/1997 | McNelis et al. |
| 5,659,934 A | 8/1997 | Jessup et al. |
| 5,681,894 A | 10/1997 | Williams et al. |
| 5,683,358 A | 11/1997 | Nielsen et al. |
| 5,693,009 A * | 12/1997 | Fox et al. .................. 604/14 |
| 5,718,675 A | 2/1998 | Leijd |
| 5,738,646 A | 4/1998 | Fox et al. |
| 5,755,906 A | 5/1998 | Achter et al. |
| 5,766,145 A | 6/1998 | Fox et al. |
| 5,772,645 A | 6/1998 | Zadini et al. |
| 5,792,096 A * | 8/1998 | Rentmeester et al. ........ 604/14 |
| 5,795,346 A | 8/1998 | Achter et al. |
| 5,800,338 A | 9/1998 | Kollerup et al. |
| 5,807,372 A | 9/1998 | Balzar |
| 5,817,047 A | 10/1998 | Osborn, III et al. |
| 5,827,251 A | 10/1998 | Moder et al. |
| 5,873,971 A | 2/1999 | Balzar |
| 5,891,127 A | 4/1999 | Moder et al. |

(56) References Cited

U.S. PATENT DOCUMENTS

| | | | |
|---|---|---|---|
| 5,911,712 A | 6/1999 | Leutwyler et al. |
| 5,928,183 A | 7/1999 | Fox et al. |
| 5,928,184 A | 7/1999 | Etheredge et al. |
| 5,947,992 A | 9/1999 | Zadini et al. |
| 5,964,741 A | 10/1999 | Moder et al. |
| 5,986,000 A | 11/1999 | Williams et al. |
| 5,986,165 A | 11/1999 | Moder et al. |
| 6,003,216 A | 12/1999 | Hull, Jr. et al. |
| 6,019,743 A | 2/2000 | Cole et al. |
| 6,039,716 A | 3/2000 | Jessup et al. |
| 6,039,828 A | 3/2000 | Achter et al. |
| 6,068,899 A | 5/2000 | Osborn, III et al. |
| 6,071,259 A | 6/2000 | Steiger et al. |
| 6,090,038 A | 7/2000 | Zunker et al. |
| 6,095,998 A | 8/2000 | Osborn et al. |
| 6,142,928 A | 11/2000 | Zunker et al. |
| 6,177,606 B1 | 1/2001 | Etheredge et al. |
| 6,177,608 B1 | 1/2001 | Weinstrauch |
| 6,180,051 B1 | 1/2001 | Schoelling |
| 6,183,436 B1 | 2/2001 | Korteweg et al. |
| 6,190,348 B1 | 2/2001 | Tiemann et al. |
| 6,191,341 B1 | 2/2001 | Shippert |
| 6,196,988 B1 | 3/2001 | Cole et al. |
| 6,206,867 B1 | 3/2001 | Osborn, III et al. |
| 6,254,565 B1 | 7/2001 | Williams et al. |
| 6,254,566 B1 | 7/2001 | Buck et al. |
| 6,264,626 B1 | 7/2001 | Linares et al. |
| 6,270,470 B1 | 8/2001 | Buck et al. |
| 6,283,952 B1 | 9/2001 | Child et al. |
| 6,299,573 B1 | 10/2001 | Hull, Jr. et al. |
| 6,302,861 B2 | 10/2001 | Tweddell, III et al. |
| 6,302,862 B1 | 10/2001 | Osborn, III et al. |
| 6,310,269 B1 | 10/2001 | Friese et al. |
| 6,358,235 B1 | 3/2002 | Osborn, III et al. |
| 6,368,442 B1 | 4/2002 | Linares et al. |
| 6,380,455 B1 | 4/2002 | Moder et al. |
| 6,416,488 B1 | 7/2002 | Jackson et al. |
| 6,419,777 B1 | 7/2002 | Achter et al. |
| 6,423,025 B1 | 7/2002 | Buzot |
| 6,432,075 B1 | 8/2002 | Wada et al. |
| 6,432,076 B1 | 8/2002 | Wada et al. |
| 6,432,246 B1 | 8/2002 | Blake |
| 6,450,986 B1 | 9/2002 | Binner et al. |
| 6,465,713 B1 | 10/2002 | Gell et al. |
| 6,478,764 B1 | 11/2002 | Suga |
| D467,599 S | 12/2002 | Brazell |
| 6,500,140 B1 | 12/2002 | Cole et al. |
| 6,508,780 B1 | 1/2003 | Edgett et al. |
| 6,511,452 B1 | 1/2003 | Rejai et al. |
| 6,570,052 B2 | 5/2003 | Zadini et al. |
| 6,572,577 B1 | 6/2003 | Binner et al. |
| D477,075 S | 7/2003 | Schoelling |
| 6,585,300 B1 | 7/2003 | Rajala et al. |
| 6,610,025 B2 | 8/2003 | Berg et al. |
| 6,645,136 B1 | 11/2003 | Zunker et al. |
| 6,648,846 B2 | 11/2003 | Binner et al. |
| 6,654,992 B2 | 12/2003 | Rajala et al. |
| 6,685,787 B2 | 2/2004 | Linares et al. |
| 6,685,788 B2 | 2/2004 | Linares et al. |
| 6,730,057 B2 | 5/2004 | Zhao et al. |
| 6,756,434 B1 | 6/2004 | Williams et al. |
| 6,773,423 B2 | 8/2004 | Osborn et al. |
| 6,830,554 B2 | 12/2004 | Jackson et al. |
| 6,958,057 B2 | 10/2005 | Berg et al. |
| 7,044,928 B2 * | 5/2006 | LeMay et al. ................ 604/15 |
| 7,081,110 B2 | 7/2006 | Karapasha |
| 7,098,292 B2 | 8/2006 | Zhao et al. |
| 7,172,573 B1 | 2/2007 | Lamb et al. |
| 7,250,129 B2 | 7/2007 | Williams et al. |
| D639,864 S | 6/2011 | Woelfel |
| D652,848 S | 1/2012 | Flanagan et al. |
| 2002/0010413 A1 | 1/2002 | Binner et al. |
| 2002/0107497 A1 | 8/2002 | Osborn et al. |
| 2002/0133135 A1 | 9/2002 | Gell et al. |
| 2002/0143287 A1 | 10/2002 | Buzot |
| 2002/0143303 A1 | 10/2002 | Intravartolo et al. |
| 2002/0147436 A1 | 10/2002 | Gell et al. |
| 2002/0151859 A1 | 10/2002 | Schoelling |
| 2002/0177835 A1 | 11/2002 | Zadini et al. |
| 2002/0183681 A1 | 12/2002 | Bernard |
| 2002/0188283 A1 | 12/2002 | Binner et al. |
| 2003/0028176 A1 | 2/2003 | Berg et al. |
| 2003/0028177 A1 | 2/2003 | Berg et al. |
| 2003/0036721 A1 | 2/2003 | Zhao et al. |
| 2003/0040695 A1 | 2/2003 | Zhao et al. |
| 2003/0055391 A1 | 3/2003 | Nguyen et al. |
| 2003/0073947 A1 | 4/2003 | Binner et al. |
| 2003/0073948 A1 | 4/2003 | Binner et al. |
| 2003/0105421 A1 | 6/2003 | Jarmon et al. |
| 2003/0125658 A1 | 7/2003 | Marvin |
| 2003/0130637 A1 | 7/2003 | Intravartolo et al. |
| 2003/0135180 A1 | 7/2003 | Nguyen et al. |
| 2003/0167048 A1 | 9/2003 | Policappelli |
| 2003/0172504 A1 | 9/2003 | Sageser et al. |
| 2003/0176844 A1 | 9/2003 | Randall et al. |
| 2003/0176845 A1 | 9/2003 | Kollwitz et al. |
| 2003/0208179 A1 | 11/2003 | Fuchs et al. |
| 2003/0208180 A1 | 11/2003 | Fuchs et al. |
| 2003/0216680 A1 | 11/2003 | Binner et al. |
| 2003/0236485 A1 | 12/2003 | Fedyk et al. |
| 2004/0054317 A1 | 3/2004 | Lemay et al. |
| 2004/0064082 A1 | 4/2004 | LeMay et al. |
| 2004/0199101 A1 | 10/2004 | LeMay et al. |
| 2004/0199102 A1 * | 10/2004 | LeMay et al. ................ 604/11 |
| 2004/0225269 A1 | 11/2004 | Zhao et al. |
| 2004/0243088 A1 * | 12/2004 | LeMay et al. ............ 604/385.18 |
| 2005/0015041 A1 | 1/2005 | Karapasha |
| 2005/0070645 A1 | 3/2005 | Williams et al. |
| 2005/0080393 A1 | 4/2005 | Policappelli |
| 2005/0177091 A1 | 8/2005 | Jarmon et al. |
| 2007/0156081 A1 | 7/2007 | Karapasha |
| 2007/0232982 A1 | 10/2007 | Jarmon et al. |
| 2007/0276317 A1 | 11/2007 | Henderson et al. |
| 2007/0293809 A1 | 12/2007 | Karapasha |

FOREIGN PATENT DOCUMENTS

| | | |
|---|---|---|
| BE | 758152 | 4/1971 |
| CA | 1086099 | 9/1980 |
| CA | 1110401 | 10/1981 |
| CA | 2024473 | 3/1991 |
| CA | 2095390 | 11/1993 |
| CA | 2143083 | 2/1996 |
| CA | 2145692 | 2/1996 |
| CA | 2153818 | 2/1996 |
| CA | 2280251 | 2/2000 |
| CA | 2302065 | 9/2000 |
| CA | 2325269 | 5/2001 |
| CA | 2325669 | 5/2001 |
| DE | 1920773 | 12/1969 |
| DE | 3328910 | 2/1985 |
| DE | 3540725 | 5/1986 |
| DE | 3609852 | 9/1987 |
| DE | 3726311 | 2/1989 |
| DE | 4446226 | 6/1995 |
| DE | 19726648 | 12/1998 |
| DE | 19747633 | 3/1999 |
| EP | 110793 | 12/1983 |
| EP | 158543 | 3/1985 |
| EP | 0243250 | 10/1987 |
| EP | 546256 | 7/1992 |
| EP | 797971 | 10/1997 |
| FR | 1515087 | 3/1968 |
| FR | 2567399 | 7/1984 |
| GB | 2097259 | 11/1982 |
| GB | 8428462 | 12/1984 |
| GB | 9419135 | 11/1994 |
| IL | 154877 | 7/2009 |
| IL | 163734 | 12/2009 |
| JP | 55-179096 | 12/1980 |
| JP | 62094156 | 4/1987 |
| JP | 04322647 | 11/1992 |
| JP | 04322648 | 11/1992 |
| JP | 5212073 | 8/1993 |

(56) References Cited

FOREIGN PATENT DOCUMENTS

| | | |
|---|---|---|
| JP | 10024064 | 1/1998 |
| JP | 2000288018 | 10/2000 |
| JP | 200117465 | 1/2001 |
| JP | 2001-145658 | 5/2001 |
| JP | 2005-531345 | 10/2005 |
| WO | 8000008 | 1/1980 |
| WO | WO 93/08779 | 5/1993 |
| WO | WO 94/15564 | 7/1994 |
| WO | 9605795 | 2/1996 |
| WO | 9637173 | 11/1996 |
| WO | 9640032 | 12/1996 |
| WO | 9806366 | 2/1998 |
| WO | 9900097 | 1/1999 |
| WO | 0037013 | 6/2000 |
| WO | 0066213 | 11/2000 |
| WO | 0197735 | 12/2001 |
| WO | 0200153 | 1/2002 |
| WO | 0202176 | 1/2002 |
| WO | 0226159 | 4/2002 |
| WO | 02074352 | 9/2002 |
| WO | 03032883 | 4/2003 |
| WO | 200400160 | 12/2003 |
| WO | 2006037157 | 4/2006 |
| WO | WO 2004/098449 | 11/2006 |
| ZA | 9305011 | 2/1994 |

OTHER PUBLICATIONS

Photocopy of box panels for O.B. Silk Ease, Personal Fit Protection.
International Search Report from PCT Application No. PCT/US2008/02934, dated Jul. 14, 2008.
Written Opinion from PCT Application No. PCT/US2008/02934, dated Jul. 14, 2008.
Examination Report dated Aug. 25, 2011 from corresponding European Application No. 04 760 601.7-1217.
Decision of Rejection dated Dec. 4, 2013 from corresponding Japanese Application No. 2009-552722.
Official Action dated Jan. 22, 2012 from corresponding Mexican Application No. MX/a/2009/009468.
Decision of Rejection mailed Dec. 11, 2012 from corresponding Japanese Application No. 2009-552722.
Official Action dated Jan. 22, 2013 from corresponding Mexican Application No. MX/a/2009/009468.
Official Notice of Final Rejection Dated February 27, 2012 From Korean Application No. 10-2009-7020746.
Notice of Reasons for Rejection dated Feb. 20, 2012 from Japanese Application No. 2009-552722.
Canadian Office Action dated Apr. 6, 2011 for corresponding Canadian Patent Application No. 2,680,144.
Office Action dated Jun. 14, 2011 from Korean Patent Application No. 10-2009-7020746.
Official Notice dated Aug. 2, 2012 from Korean Application No. 10-2009-7020746.
Notification of the First Office Action dated Apr. 6, 2012 from Chinese Application No. 200880014388.3.
Korean Office Action dated Aug. 2, 2012 for corresponding Korean Patent Application No. 10-2009-7020746 with English summary.
European Search Report dated Apr. 27, 2011 for corresponding European Patent Application No. 04760601.7.
English translation of First Office Action dated Apr. 6, 2012 for corresponding Chinese Patent Application No. 20088014388.3. (Office Action and English summary of Office Action previously cited on Sep. 14, 2012.
Notification of the Second Office Action dated Nov. 30, 2012 from corresponding Chinese Application No. 200880014388.3.
Supplementary European Search Report dated Dec. 17, 2012 from corresponding European Application No. 08726462.8.
Israeli Office Action for corresponding Israeli Patent Application No. 200734 with English summary dated Apr. 5, 2011.

* cited by examiner

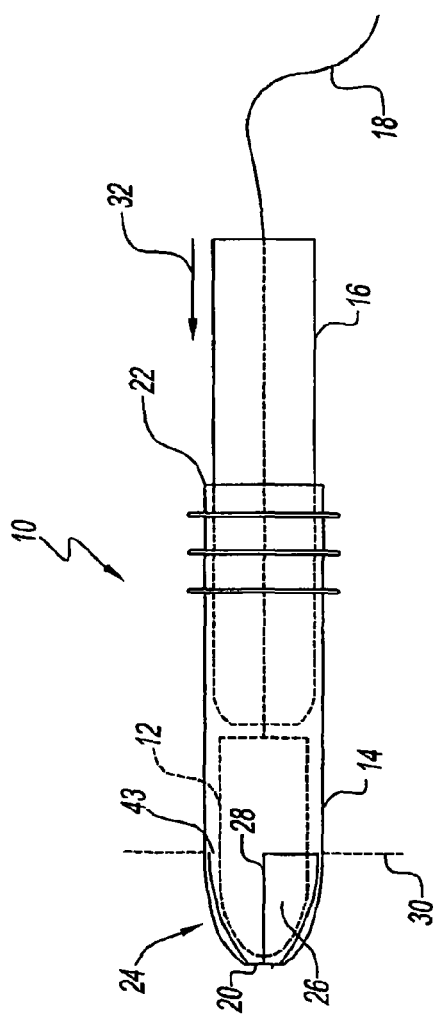
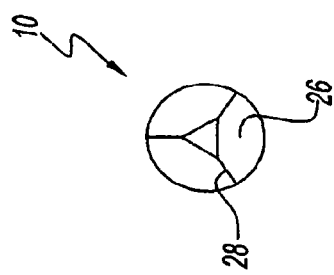

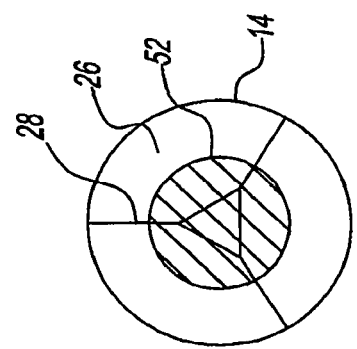
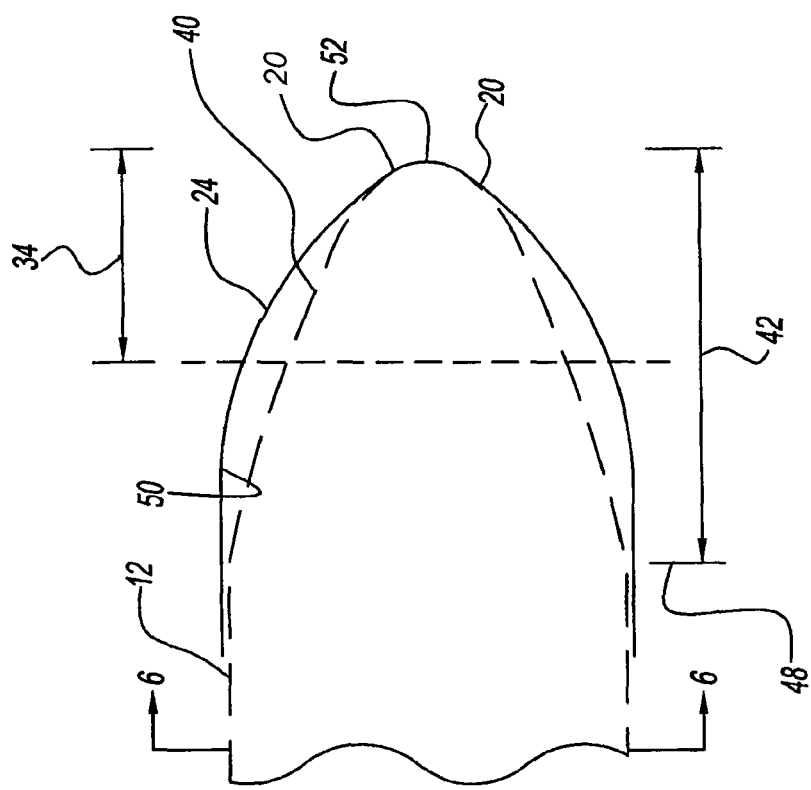

TAMPON ASSEMBLY HAVING SHAPED PLEDGET

RELATED APPLICATIONS

This application is a continuation-in-part application of pending U.S. patent application Ser. No. 10/834,386, filed Apr. 28, 2004, which claims the benefit of U.S. Provisional Application Ser. No. 60/467,482, filed May 2, 2003, the contents each being incorporated by reference herein in their entirety.

BACKGROUND OF THE INVENTION

1. Field of the Invention

The present invention is generally related to a tampon assembly. More particularly, the present invention is related to a tampon assembly having an applicator barrel with no more than three petals.

2. Description of Related Art

A tampon assembly is used to inject an absorbent or hygienic material, known as a tampon pledget, into the vaginal vault. The pledget of commercial tampon assemblies is typically positioned in a barrel for expulsion from a barrel by a plunger. The use of such assemblies requires a user to insert an end of the barrel into the vaginal vault.

Once the barrel has been inserted, the plunger can be used to expel the pledget from the end of the barrel into the vaginal vault. Once the pledget is in position, the pledget expands upon contact with moisture to conform to contours of the body and, thus, provide leakage protection. Comfort to the user during insertion of the barrel and expulsion of the pledget is an important aspect for the commercial success of the tampon assembly. Furthermore, perceived and actual level of performance is also dependent how comfortable the applicator is to insert into the user's body.

Many attempts have been made to increase the comfort associated with the use of tampon assemblies. For example, the barrels of some tampon assemblies include a dome shaped end. The dome shaped end includes a number or plurality of shaped petals configured to open during expulsion of the pledget. Unfortunately, the petals themselves can be a source of discomfort. An applicator with too many petals can pinch the vaginal vault during insertion or create a perception by the user that the petals will pinch the vaginal vault during insertion. Moreover, too few petals increase petal resistance during expulsion of the pledget from the barrel causing insertion difficulty.

Additionally, in prior assemblies having blunt or unshaped pledgets, users often push the pledget as far into the applicator tip as possible prior to insertion of the applicator. However, this can cause the petals to open prematurely, namely before insertion of the barrel into the body. The open petals provide prior barrels with a "claw-like" insertion tip, which can scratch during insertion of the barrel. Also, the open petals can close during the insertion process, which can pinch the skin of the user.

Accordingly, there is a continuing need for a tampon assembly that is aesthetically pleasing to a user and also has a quantity of petals that increases comfort to the user while having a petal resistance within a desirable range.

SUMMARY OF THE INVENTION

The present disclosure provides a tampon assembly having an applicator with a maximum of three petals on the insertion tip.

The present disclosure also provides such a tampon assembly having an applicator with a tapered insertion tip.

The present disclosure further provides such a tampon assembly having a shaped and/or tapered pledget.

The present disclosure still further provides such a tampon assembly having a tapered insertion tip that has some portion of its inner surface supported by a shaped pledget.

The present disclosure yet further provides such a tampon assembly that has an applicator barrel that is easy to insert, and a shaped pledget that gradually opens the petals of the barrel.

These and other advantages and benefits of the present disclosure are provided by a tampon applicator assembly having an applicator barrel with an insertion tip having a maximum of three petals. Additionally, the tampon applicator assembly can be provided with a tapered insertion tip. A shaped pledget can be housed in the applicator barrel, which provides support to the petals.

The above-described and other advantages and features of the present disclosure will be further appreciated and understood by those skilled in the art from the following exemplary detailed description and drawings.

BRIEF DESCRIPTION OF THE DRAWINGS

FIG. 1 is a side view of an exemplary embodiment of a tampon assembly according to the present disclosure;

FIG. 2 is an end view of the assembly of FIG. 1.

FIG. 5 is an exemplary embodiment of an insertion tip having a shaped pledget according to the present invention disclosure.

FIG. 6 is a view taken along lines 6-6 in FIG. 5.

DETAILED DESCRIPTION OF THE INVENTION

Figure 3:
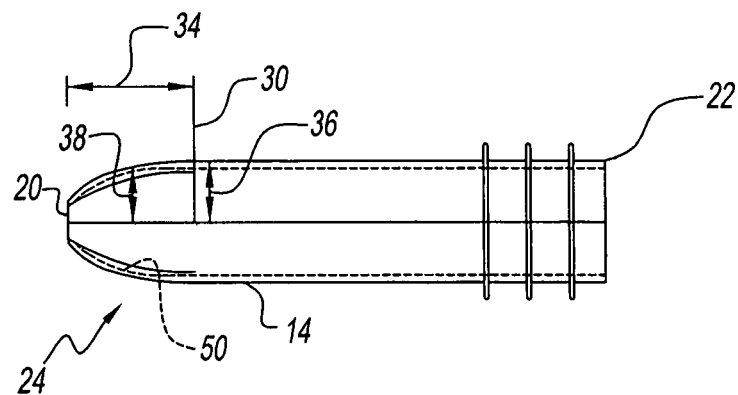
FIG. 3 is a side view of the barrel of FIG. 1.

Through consumer testing it has been unexpectedly found that a tampon applicator having an insertion tip with three petals is most preferred over those tampon applicators with an insertion tip having greater than three petals. In lieu of this unexpected discovery, a tampon applicator with no more than three petals is provided, which overcomes all prior art drawbacks, including those noted above.

Generally, the present disclosure provides a tampon applicator assembly having an applicator barrel with an insertion tip having no more than three petals.

In one embodiment, the present disclosure provides a tampon applicator assembly having an applicator barrel with a tapered insertion tip and a shaped pledget housed in the applicator barrel. The tapered insertion tip has a maximum of three petals, which are supported by the shaped pledget housed in the barrel.

Referring now to the drawings and more particularly to FIGS. 1 and 2, an exemplary embodiment of a tampon assembly generally represented by reference numeral 10 is illustrated. Assembly 10 has a shaped pledget 12, a barrel 14, and a plunger 16. Shaped pledget 12 can include a withdrawal cord 18 connected thereto, which extends out of assembly 10.

Shaped pledget 12 is disposed in barrel 14 and significantly improves the performance of assembly 10 as compared to prior assemblies having a blunt or squared-off pledget.

Barrel 14 has a first end 20 and a second end 22. First end 20 defines an insertion tip 24 having three petals 26. Petals 26 are defined at first end 20 by a number or plurality of slits 28. The number of slits 28 typically corresponds to the number of petals 26 present. Insertion tip 24 terminates at a plane 30 defined at a root or base 43 of petals 26 (e.g., the bottom of slits 28). Base 43 of petals 26 may have hinges to pivot each of petals 26 into or out of barrel 14 along each hinge.

Plunger 16 is useable to expel pledget 12 from barrel 14. Plunger 16 is slideably disposed in barrel 14 at second end 22. Pledget 12 is expelled through first end 20 through the movement of plunger 16 in the direction of arrow 32. As plunger 16 moves in the direction of arrow 32, the plunger can urge pledget 12 into petals 26 until the petals open along slits 28 and the pledget is expelled from barrel 14 through insertion tip 24.

Referring to FIG. 3, insertion tip 24 has a length 34, an outer radial dimension 36, and an inner radial dimension 38. Preferably, barrel 14 has a minimal thickness such that inner and outer dimensions 36, 38, respectively, can be considered to be substantially similar.

Length 34 is defined as the distance between first end 20 and plane 30. Insertion tip 24 is, preferably, tapered or elliptical in shape. Specifically, dimensions 36, 38 decrease along length 34, linearly or non-linearly, from a maximum at plane 30 to a minimum at first end 20.

The taper of insertion tip 24 is defined as a ratio of the maximum radial dimension of insertion tip 24, namely radial dimension 36 at plane 30, divided by length 34. In one embodiment of the present disclosure, insertion tip 24 has a taper ratio of more than about 0.3 to less than 1.0. In another embodiment, insertion tip 24 has a taper ratio of more than about 0.4 to less than about 0.8. In yet another embodiment, insertion tip 24 has a taper ratio of about 0.4 to about 0.5. Both qualitative and quantitative consumer testing has shown that an insertion tip 24 that tapers gently towards the first end 20 is preferred for insertion ease, insertion comfort, and pledget placement in the vaginal vault.

Figure 4:
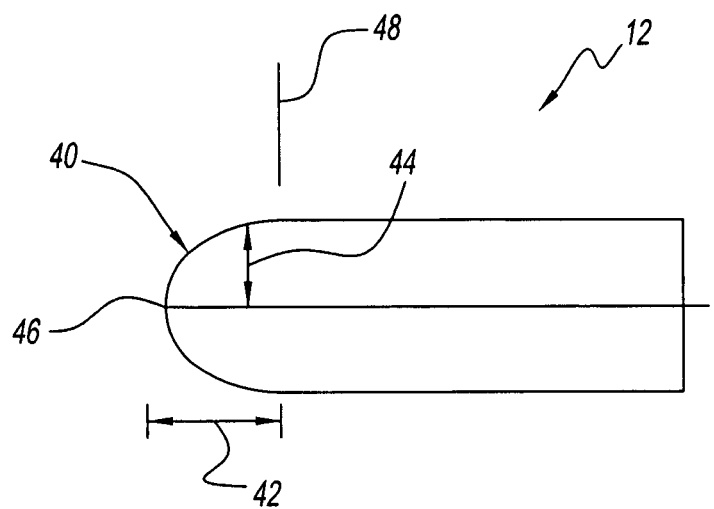
FIG. 4 is a side view of the shaped pledget of FIG. 1.

It has been determined that the perceived and actual level of comfort of assembly 10 can be enhanced through the use of shaped pledget 12, shown in FIG. 4, for supporting petals 26 of insertion tip 24.

Pledget 12 has a tip section 40 that is, preferably, shaped to support insertion tip 24. Tip section 40 has a length 42 and an outer radial dimension 44 that decreases or is tapered along length 42. Length 42 is defined as the distance between a front end 46 of pledget 12 and a plane 48. Plane 48 is defined as a plane through pledget 12 where the taper of tip section 40 begins.

Tip section 40 supports or contacts (hereinafter "supports") an inner surface area 50 of insertion tip 24 to provide increased comfort as compared to prior assemblies. Inner surface area 50 is defined as the surface area of tip 24 between first end 20 and plane 30.

Tip section 40 supports a portion 52 of inner surface area 50. Portion 52 is considered to be "supported" by tip section 40 when outer dimension 44 is at least about 75% of inner dimension 38. In another embodiment of the present disclosure, outer dimension 44 is at least about 85% of inner dimension 38. In yet another embodiment, outer dimension 44 is about 100% of inner dimension 38.

Referring now to FIGS. 5 and 6, an exemplary embodiment of portion 52 supported by tip section 40 is illustrated. Tip section 40 of pledget 12 is illustrated supporting portion 52, which begins at first end 20 and runs along inner surface area 50 towards plane 30. In this embodiment, pledget 12 supports petals 26 at least at first end 20. It is contemplated that portion 52 support at least about 10% of inner surface area 50. In another embodiment of the present disclosure, portion 52 supports at least about 50% of inner surface area 50. In yet another embodiment, portion 52 supports about 100% of inner surface area 50.

Tip section 40, most preferably, has a shape closely matching a shape of insertion tip 24 to provide proper support for petals 26. The taper ratio of tip section 40, preferably, matches the shape of insertion tip 24, and external diameters of tip section 40 should be slightly less than inner radial dimension 38 of insertion tip 24. If the taper ratio of tip section 40 is less than the taper ratio of insertion tip 24, tip section 40 may not be fully supported. If the taper ratio of tip section 40 exceeds the taper ratio of insertion tip 24, insertion tip 24 may not be fully supported, and pledget 12 may be pushed up into insertion tip 24. Pledget 12 being pushed up into insertion tip 24 may cause petals 26 to pre-open leading to pinching and perceived and actual discomfort on insertion of tampon applicator assembly 10.

Insertion tip 24 has a tip volume or a void defined by petals 26 and plane 30. In one embodiment of the present disclosure, shaped pledget 12 occupies at least about 50% of the volume of insertion tip 24 measured when tip section 40 is pushed as far into the insertion tip as possible without deforming petals 26. In another embodiment, shaped pledget 12 occupies at least about 75% of the volume of insertion tip 24 measured when tip section 40 is pushed as far into the insertion tip as possible without deforming petals 26. In yet another embodiment, shaped pledget 12 occupies at least about 90% of the volume of insertion tip 24 measured when tip section 40 is pushed as far into the insertion tip as possible without deforming petals 26.

When shaped pledget 12 has a taper ratio (e.g., dimension 44 divided by dimension 42) that is greater than the taper ratio of insertion tip 24, length 42 of shaped pledget 12 should occupy at least about 50% of length 34 of insertion tip. In one embodiment, length 42 of shaped pledget 12 occupies at least about 75% of length 34 of insertion tip 24. In another embodiment, length 42 of shaped pledget 12 occupies at least about 90% of length 34 of insertion tip 24.

When shaped pledget 12 has a taper ratio that is less than the taper ratio of insertion tip 24, dimension 44 of shaped pledget 12 at any given point along its length 42 should be at least about 50% of the dimension 38 of applicator tip 24 at the corresponding point. In one embodiment, dimension 44 of shaped pledget 12 at any given point along its length 42 is at least about 75% of the dimension 38 of applicator tip 24 at the corresponding point. In another embodiment, dimension 44 of shaped pledget 12 at any given point along its length 42 is at least about 90% of the dimension 38 of applicator tip 24 at the corresponding point. As a result, a void volume or unoccupied tip volume is reduced.

Advantageously, shaped pledget 12 prevents forces on insertion tip 24 applied during insertion of barrel 14 into the body from collapsing petals 26 inward towards the pledget. Further, shaped pledget 12 enables the petals 26 to be made thinner to decrease the expulsion force while still mitigating the collapse or deflection of petals 26. In one embodiment of the present disclosure the petals have a thickness between about 0.005 inches to about 0.03 inches, and any range therebetween. In a preferred embodiment, the petals have a thickness between about 0.006 inches to about 0.013 inches. In another preferred embodiment, the petals have a thickness between about 0.008 inches to about 0.011 inches.

Shaped pledget 12 also has been found to reduce instances of pinching and scratching by petals 26 during insertion of barrel 14. Since shaped pledget 12 supports surface area 50, assembly 10 mitigates instances of pinching and scratching.

Assembly 10 has been found to increase comfort of use during both the insertion of barrel 14 and the expulsion of pledget 12. First, the taper ratio of insertion tip 24 facilitates insertion comfort by gradually parting the vulva-vaginal channel over a longer length of the barrel as compared to prior blunt ended barrels. In addition, tip section 40 of pledget 12 gradually opens petals 26 over a longer length of the pledget as compared to prior blunt ended pledgets.

Moreover, a supported "wedge" action at an initial insertion point into the vaginal vault is created. The wedge action is initially created during insertion by the tapered insertion end of the applicator that facilitates insertion comfort by gradually parting the vagina. The wedge action is simultaneously recreated as the tapered shaped pledget is expelled from the tapered applicator into the vaginal vault. Therefore, tampon assembly 10 reduces petal pinching and increases perceived and actual comfort during insertion of both the applicator and subsequent expulsion of the shaped pledget. Moreover, the tapered pledget insertion tip 24 successfully supports, guides, and places shaped pledget 12, after expulsion from barrel 14, into a desired vaginal location.

These improved properties permit insertion tip 24 to have only three or fewer petals 26 with an ejection force within a desirable range to overcome petal resistance, reduce overall insertion forces and resistance, and reduce initial insertion membrane resistance.

Surprisingly, the applicator barrel having at most only three petals according to the present disclosure requires an ejection force to expel the shaped pledget from the barrel of less than about 50 ounces. In one embodiment, the ejection force required to expel the pledget from the barrel is between about 5 ounces to about 35 ounces. In another embodiment, the ejection force required to expel the shaped pledget from the barrel is between about 8 ounces to about 25 ounces.

The ejection force may be measured by any suitable procedure known in the art. By way of example, the ejection force may be measured as follows. A totally assembled tampon with post-formed petals is used in the test. A Weigh-Tronix™ scale (Model #WI-130 or equivalent) is used. The scale is tared. The weights are recorded in ounces. The applicator is grasped by the finger grip using the thumb and the middle finger. With the plunger end down, the applicator is placed on the top of the balance platform and a steady downward motion is applied until the pledget is ejected from the applicator barrel. The maximum ejection force indicated by the scale is recorded. Generally, the mean and standard deviation is determined for at least five samples.

Tip section 40 of pledget 12 can be shaped by compressing the tip to a higher density than the rest of the pledget. Alternately, tip section 40 can be shaped providing the tip with a less dense material that, when compressed, provides the tip with the same density as the rest of the pledget. In addition, tip section 40 of pledget 12 can be shaped by cutting or trimming the tip to the desired shape so that the tip has the same density as the rest of the pledget. Of course, combinations of one or more of the aforementioned methods is contemplated by the present disclosure.

Suitable materials for forming shaped pledget 12 include, for example, cellulosic; rayon; cotton; pulp; superabsorbent, such as Oasis; absorbent foam, such as hydrophilic polyurethane foam; or any combinations thereof.

Suitable materials for forming barrel 14 and/or plunger 16 include, for example, biopolymer, cardboard, heat shrink plastic, paper slurry, plastic, plastic tubing, pulp slurry, pulp-molded paper, or any combinations thereof.

In one embodiment of the present disclosure, barrel 14 can be formed of low-density polyethylene (LDPE), and plunger 16 can be formed of axially oriented high-density polyethylene (HDPE). It has also been discovered through consumer testing that consumers prefer a tampon assembly fabricated from a softer resin. Therefore, barrel 14 and/or plunger 16 may include a blend of about 0 wt. % to about 100 wt. % LDPE and about 100 wt. % to about 0 wt. % thermoplastic elastomer (TPE). In another preferred embodiment, barrel 14 and/or plunger 16 are formed from a blend comprising about 50% to about 90% LDPE and about 50% to about 10% TPE. In another preferred embodiment, barrel 14 and/or plunger 16 are formed from a blend comprising about 80% LDPE and about 20% TPE.

In another embodiment according to the present disclosure, a preferred TPE to use is a tri-block (terpolymer), having an A-B-A configuration of monomers, in which monomer B is not the same as monomer A. Preferred monomer blocks are styrene, butadiene (or isoprene), and styrene. There are also other classes of thermoplastic elastomers that one could use. These include, for example, thermoplastic polyurethane elastomers and others. These and other classes are described in a book entitled *Thermoplastic Elastomers: A Comprehensive Review*, ed. N. R. Legge, G. Holden and H. E. Schroeder, Munich: Hanser, 1987, the disclosure of which is incorporated in its entirety by reference herein. Examples of other suitable resins that may be used in the present disclosure are described in co-owned U.S. Pat. Nos. 5,681,894; 5,986,000; 6,254,565; and 6,756,434, as well as related published Patent Application US 2005/0070645 A1; the disclosures of which are incorporated in their entirety by reference herein.

Other additives could also be added to the polyolefins to provide specific benefits, such as greater thermal stability, greater flexibility, higher lubricity, anti-static behavior, greater latitude of processing, colorants, and so on. Such additives would be familiar to those skilled in the art of polymer and thermoplastic formulations. Examples are provided in standard texts, for example, *Additives for Plastics*, ed. J. Thuen, published by D.A.T.A. Inc. the International Plastics Selector, 1987. Another text is the *Plastics Compounding Redbook for Resin Producers, Formulators and Compounders*, published annually by Advanstar Communications, Cleveland, Ohio, ed. La Verne Leonard.

In addition, barrel 14 and/or plunger 16 may be coated with a coating material to reduce friction and/or increase strength. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

It should be recognized that pledget 12, barrel 14, and/or plunger 16 can have any cross-sectional shape, such as circular and non-circular, including oval or polygonal shapes. Furthermore, it is contemplated by the present disclosure for the cross-sectional shape to vary along the length of pledget 12, barrel 14, and/or plunger 16.

It should also be noted that the terms "first", "second", and "third" and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the scope thereof.

What is claimed is:
1. A tampon assembly, comprising:
 a barrel region having a single layer plastic tubular wall having an inner surface and an outer surface, said barrel region having a first end and a second end, said barrel region having a plurality of discrete petals at said first end that define a generally tapered shaped insertion tip region, said discrete petals being separated from each other by a plurality of cuts that form a break of material through said tubular wall, each of said plurality of cuts having a terminal end adjacent a base region of said plurality of discrete petals, each of said plurality of cuts extending along said barrel region for a first length measured from said first end to said terminal end;

a tapered pledget having an end region that has been compressed to form a tapered insertion tip that has a greater density than an adjacent region of said pledget prior to said tampon assembly being inserted into a user, said tapered tip having a length that is less than said first lengths of said plurality of cuts, said tapered tip contacting and supporting at least said base regions of said plurality of petals adjacent to said terminal ends of said plurality of cuts while said tampon assembly is being inserted into said body for mitigating against said plurality of petals pinching said user.

2. The tampon assembly according to claim 1, wherein said insertion tip region has a first taper ratio between about 0.3 to less than 1.0.

3. The tampon assembly according to claim 1, wherein said tapered pledget has a second taper ratio approximately equal to said first taper ratio.

4. The tampon assembly according to claim 1, wherein said second taper ratio is greater than said first taper ratio.

5. The tampon assembly according to claim 1, wherein said second taper ratio is less than said first taper ratio.

6. The tampon assembly according to claim 1, wherein said tapered tip has a density that is greater than a density of a remaining portion of said pledget.

7. The tampon assembly according to claim 1, wherein said pledget comprises a material selected from the group consisting of rayon, cotton, pulp, superabsorbent, absorbent foam, and any combinations thereof.

8. The tampon assembly of claim 1, wherein said tapered insertion tip region is generally elliptical in shape.

9. A tampon assembly comprising:
a barrel region having a single layer plastic tubular wall having an inner surface and an outer surface and forming a first end and a second end, said barrel region having a plurality of discrete petals at said first end that define a generally tapered insertion tip region, said discrete petals being separated from each other by a plurality of cuts that form a break of material through said tubular wall, each of said plurality of cuts having a terminal end adjacent a base region of said plurality of discrete petals, each of said plurality of cuts extending along said barrel region for a first length measured from said first end to said terminal end; and
a tapered pledget having a insertion end region that has been compressed to form a tapered shaped insertion tip that has a greater density than an adjacent region of said pledget prior to said tampon assembly being inserted into a user, said tapered tip having a length that is less than said first lengths of said plurality of cuts, said tapered tip contacting and supporting at least said base regions of the plurality of petals adjacent to said terminal ends of said plurality of cuts while said tampon assembly is being inserted into said user for mitigating against said plurality of petals pinching said user
wherein said barrel region having said tapered insertion tip provides a first long length that enables gradual insertion of said barrel region,
wherein, prior to ejection from said barrel region, (i) said barrel encloses said tapered pledget and (ii) an outer surface of said tapered pledget contacts and supports said petals at said first end prior to ejection of said pledget through said plurality of discrete petals.

10. The tampon assembly according to claim 9, wherein said insertion tip region has a first taper ratio of greater than about 0.3 to less than 1.0.

11. The tampon assembly according to claim 10, wherein said tapered tip has a second taper ratio that is less than, greater than or equal to said first taper ratio.

12. The tampon assembly according to claim 9, wherein said pledget comprises a material selected from the group consisting of rayon, cotton, pulp, superabsorbent, and any combinations thereof.

13. The tampon assembly according to claim 9, wherein said tapered tip has a density that is greater than or substantially equal to a density of a remaining portion of said pledget.

14. The tampon assembly of claim 9, wherein said tapered insertion tip region is generally elliptical in shape.

15. A tampon assembly comprising:
a barrel region having a single layer plastic tubular wall having an inner surface and an outer surface and forming a first end and a second end, said barrel region having a plurality of discrete petals at said first end that define a generally tapered insertion tip region, said discrete petals being separated from each other by a plurality of cuts that form a break of material through said tubular wall, each of said plurality of cuts having a terminal end adjacent a base region of said plurality of discrete petals, each of said plurality of cuts extending along said barrel region for a first length measured from said first end to said terminal end; and
a generally tapered pledget housed in said barrel, said tapered pledget having an outer surface, and a tapered tip having a length that is less than said first lengths of the plurality of cuts, said tapered tip contacting and supporting at least said base regions of said plurality of petals adjacent to said terminal ends of said plurality of cuts while said tampon assembly is being inserted into a user for mitigating against said plurality of petals pinching said user,
wherein said pledget is ejectable from said barrel region with an ejection force of greater than about 5 ounces less than about 8 ounces.

16. The tampon assembly of claim 15, wherein said plurality of discrete petals have a petal thickness between about 0.005 inches and about 0.03 inches.

17. The tampon assembly of claim 15, wherein said plurality of discrete petals have a petal thickness between about 0.006 inches and about 0.013 inches.

18. The tampon assembly of claim 15, wherein said barrel region is formed form a composition comprising a blend of about 0 wt. % to about 100 wt. % low-density polyethylene and about 100 wt. % to about 0 wt. % thermoplastic elastomer, based on a total weight of the composition.

19. The tampon assembly of claim 15, wherein said barrel region is formed from a composition comprising a blend of about 50 wt. % to about 90 wt. % low-density polyethylene and about 50 wt. % to about 10 wt. % thermoplastic elastomer, based on a total weight of the composition.

20. The tampon assembly of claim 15, wherein said barrel region is formed form a composition comprising about 80 wt. % low-density polyethylene and about 20wt. % thermoplastic elastomer, based on a total weight of the composition.

21. The tampon assembly of claim 15, wherein said tapered insertion tip region is generally elliptical in shape.

22. A tampon assembly, comprising:
a barrel region having a single layer plastic tubular wall forming a first end and a second end, said barrel having a plurality of discrete petals at said first end that form an insertion tip region, said petals being formed by a plurality of cuts that form a break of material through said tubular wall, said petals having an inner surface, each of the plurality of cuts having a terminal end adjacent a base region of said plurality of discrete petals, each of said plurality of cuts extending along said barrel region for a first length measured from said first end to said terminal end, said insertion tip having an inner surface, said insertion tip region having a first taper ratio defined as a radius of said barrel at said base region divided by a length of said insertion tip region, said first taper ratio being more than about 0.3 to less than about 1.0 throughout said insertion tip region;
a plunger being slidably received in said barrel region; and
a tapered pledget having an insertion end region that has been compressed to form a tapered insertion tip, said tapered tip having a length that is less than said first lengths of said plurality of cuts,
wherein said tapered tip contacts and supports at least the base regions of said plurality of petals adjacent to the terminal ends of said plurality of cuts while said tampon assembly is being inserted into said body for mitigating against said plurality of petals pinching a user,
wherein said tapered tip of said pledget has an outer radial dimension that decreases between a distal tip end of said pledget and a plane through said pledget where said taper begins,
wherein said pledget has a second taper ratio of said outer radial dimension at said plane to a length of said tapered tip between said tip end and said second plane, of more than about 0.3 and less than about 1.0.

23. The tampon assembly of claim 22, wherein said tapered insertion tip region is generally elliptical in shape.

24. The tampon assembly according to claim 22, wherein said second taper ratio is approximately equal to said first taper ratio.

25. The tampon assembly according to claim 22, wherein said second taper ratio is greater than said first taper ratio.

26. The tampon assembly according to claim 22, wherein said second taper ratio is less than said first taper ratio.

27. A tampon assembly, comprising:
a barrel region having a single layer plastic tubular wall forming a first end and a second end, said barrel region having a plurality of discrete petals at said first end that form an insertion tip region, said petals being separated from each other by a plurality of cuts that form a break of material through said tubular wall of said barrel region, said petals having an inner surface said petals having an inner surface, each of said plurality of cuts having a terminal end adjacent a base region of said plurality of discrete petals, each of said plurality of cuts extending along said barrel region for a first length measured from said first end to said terminal end, said insertion tip region having a first taper ratio defined as a radius of said barrel at said base region divided by a length of said insertion tip region, said first taper ratio being more than about 0.3 to less than about 1.0 throughout said insertion tip region;
a plunger being slidably received in said barrel region; and
a tapered pledget having an insertion end region that has been compressed to form a tapered insertion tip, said tapered tip having a length that is less than said first lengths of said plurality of cuts, said tapered tip contacting and supporting at least said base regions of said plurality of petals adjacent to said terminal ends of said plurality of cuts while said tampon assembly is being inserted into said body for mitigating against said plurality of petals pinching a user.

28. The tampon assembly of claim 27, wherein said tapered insertion tip region is generally elliptical in shape.

29. The tampon assembly according to claim 27, wherein said tapered tip of said pledget has an outer radial dimension that decreases between a front end of said pledget and a plane through said pledget where said taper begins, wherein said pledget has a second taper ratio of said outer radial dimension at said plane to a length of said tapered tip between said tip end and said plane.

30. The tampon assembly according to claim 29, wherein said tapered pledget has a second taper ratio that is approximately equal to said first taper ratio.

31. The tampon assembly according to claim 29, wherein said second taper ratio is greater than said first taper ratio.

32. The tampon assembly according to claim 29, wherein said second taper ratio is less than said first taper ratio.

33. The tampon assembly according to claim 29, wherein said second taper ratio is more than about 0.3 to less than about 1.0 throughout said insertion tip.

34. A tampon assembly, comprising:
a barrel region having a single layer plastic tubular wall forming a first end and a second end, said barrel region having a plurality of discrete petals at said first end that form an insertion tip region, said petals being separated from each other by a plurality of cuts that form a break of material through said tubular wall of said barrel region, said petals having an inner surface said petals having an inner surface, each of said plurality of cuts having a terminal end adjacent a base region of said plurality of discrete petals, each of said plurality of cuts extending along the barrel region for a first length measured from said first end to the terminal end, said insertion tip region having a first taper ratio defined as a radius of said barrel at said base region divided by a length of said insertion tip region;
a plunger being slidably received in said barrel; and
a tapered pledget having an insertion end region that has been compressed to form a tapered insertion tip of said pledget prior to said tampon assembly being inserted into a user, said tapered tip region having a length that is less than said first lengths of said plurality of cuts, said tapered tip region contacting and supporting at least said base regions of said plurality of petals adjacent to said terminal ends of said plurality of cuts while said tampon assembly is being inserted into a user for mitigating against said plurality of petals pinching said user, said tapered tip of said pledget having an outer radial dimension that decreases between a distal tip end of said pledget and a second plane through said pledget where said taper begins,
wherein said pledget has a second taper ratio of said outer radial dimension at said second plane to a length of said tapered tip between said tip end and said second plane of more than about 0.3 and less than about 1.0.

35. The tampon assembly of claim 34, wherein said tapered insertion tip region is generally elliptical in shape.

36. The tampon assembly according to claim 34, wherein said first taper ratio is more than about 0.3 to less than about 1.0 throughout said insertion tip region.

37. The tampon assembly according to claim 34, wherein said second taper ratio is greater than said first taper ratio.

38. The tampon assembly according to claim 34, wherein said second taper ratio is less than said first taper ratio.

39. A tampon assembly, comprising:
a barrel region having a single layer tubular wall having an inner surface and an outer surface, said barrel region having a first end and a second end, said barrel region having a plurality of discrete petals at said first end that define a generally tapered shaped insertion tip region, said discrete petals being separated from each other by a plurality of cuts that form a break of material through said tubular wall, each of said plurality of cuts having a terminal end adjacent a base region of said plurality of discrete petals, each of said plurality of cuts extending along said barrel region for a first length measured from said first end to said terminal end,
a tapered pledget having an end region that has been compressed to form a tapered insertion tip of the pledget prior to said tampon assembly being inserted into a user, said tapered tip region having a length that is less than said first lengths of the plurality of cuts, said tapered tip region contacting and supporting at least said base regions of said plurality of petals adjacent to said terminal ends of said plurality of cuts while said tampon assembly is being inserted into said user for mitigating against the plurality of petals pinching said user,
wherein said barrel region has a composition comprising a blend of about 0 wt. % to about 100 wt. % low-density polyethylene and about 100 wt. % to about 0 wt. % thermoplastic elastomer, based on a total weight of the composition.

40. The tampon assembly of claim 39, wherein said barrel region is formed from a composition comprising a blend of about 50 wt. % to about 90 wt. % low-density polyethylene and about 50 wt. % to about 10 wt. % thermoplastic elastomer, based on a total weight of said composition.

41. The tampon assembly of claim 39, wherein said barrel region is formed form a composition comprising about 80 wt. % low-density polyethylene and about 20 wt. % thermoplastic elastomer, based on a total weight of said composition.

* * * * *